US008462343B2

(12) United States Patent
Rao et al.

(10) Patent No.: US 8,462,343 B2
(45) Date of Patent: Jun. 11, 2013

(54) WIRELESS SENSOR SYSTEM FOR ENVIRONMENTAL MONITORING

(75) Inventors: Govind Rao, Columbia, MD (US); Yordan Kostov, Columbia, MD (US)

(73) Assignee: University of Maryland Baltimore County, Baltimore, MD (US)

( * ) Notice: Subject to any disclaimer, the term of this patent is extended or adjusted under 35 U.S.C. 154(b) by 114 days.

(21) Appl. No.: 13/001,416

(22) PCT Filed: Jun. 29, 2009

(86) PCT No.: PCT/US2009/049047
§ 371 (c)(1),
(2), (4) Date: Dec. 24, 2010

(87) PCT Pub. No.: WO2009/158702
PCT Pub. Date: Dec. 30, 2009

(65) Prior Publication Data
US 2011/0235041 A1    Sep. 29, 2011

Related U.S. Application Data

(60) Provisional application No. 61/133,343, filed on Jun. 27, 2008.

(51) Int. Cl.
*G01N 21/00* (2006.01)
(52) U.S. Cl.
CPC .................................... *G01N 21/00* (2013.01)
USPC .......................................... 356/432; 356/436
(58) Field of Classification Search
CPC ...................................................... G01N 21/00
USPC ................................................... 356/437–440
See application file for complete search history.

(56) References Cited

U.S. PATENT DOCUMENTS

| 3,603,952 | A  | * | 9/1971  | Smith ........................ 340/539.26 |
| 5,208,465 | A  | * | 5/1993  | Jacobson ........................ 250/573 |
| 5,364,297 | A  |   | 11/1994 | Rohardt |
| 5,461,236 | A  | * | 10/1995 | Gram et al. ................ 250/461.1 |
| 5,816,874 | A  | * | 10/1998 | Juran et al. ........................ 441/1 |
| 5,929,453 | A  | * | 7/1999  | Andrews et al. ........... 250/461.1 |
| 6,840,121 | B2 | * | 1/2005  | Thomas et al. ............. 73/863.31 |
| 7,269,537 | B1 | * | 9/2007  | Mattern ........................ 702/190 |
| 2003/0037602 | A1 | * | 2/2003  | Glasgow et al. ............. 73/61.41 |
| 2004/0130713 | A1 | * | 7/2004  | O'Mongain ................. 356/300 |
| 2004/0257264 | A1 |   | 12/2004 | Moeller-Jensen |
| 2006/0181425 | A1 |   | 8/2006  | Crane et al. |
| 2007/0078610 | A1 | * | 4/2007  | Adams et al. .................... 702/28 |

FOREIGN PATENT DOCUMENTS

WO    WO2005026053 A2    3/2005

OTHER PUBLICATIONS

Written Opinion of the International Searching Authority for PCT/US2009/049047, mailed Mar. 19, 2010.
International Search Report for PCT/US2009/049047, mailed Mar. 19, 2010.

* cited by examiner

*Primary Examiner* — Michael P Stafira
(74) *Attorney, Agent, or Firm* — Rene A. Vazquez, Esq.

(57) ABSTRACT

A wireless sensor system is provided that utilizes reliable, small, inexpensive and low power-consuming sensor nodes for monitoring environmental parameters that can communicate through wireless transmitters to a base station. The sensor nodes preferably incorporate anti-biofouling protection, so as to withstand continuous field deployment in streams and/or riparian areas.

24 Claims, 19 Drawing Sheets

PD – photodiode, FG – Frequency generator, ⊗ - multiplier, µC – microcontroller, Tx – transmitter, Phase shift and demodulation of the fluorescence of immobilized RuDPBP at different frequencies. ■ – air, ▲ - $N_2$ DM- dichroic mirror, F – filter, M – directing mirror.

| Code | Sensor | Light source | Photodetector |
|---|---|---|---|
| 000 | Optical density | OD LED | OD signal photodiode |
| 001 | pH | pH blue LED | pH photodetector |
| 010 | pH | pH violet LED | pH photodetector |
| 011 | Oxygen | Oxygen blue LED In-phase | Oxygen photodetector |
| 100 | Oxygen | Oxygen orange LED In-phase | Oxygen photodetector |
| 101 | Oxygen | Oxygen blue LED Quadrature | Oxygen photodetector |
| 110 | Oxygen | Oxygen orange LED Quadrature | Oxygen photodetector |
| 111 | Optical density | OD LED | OD reference photodiode |

WIRELESS SENSOR SYSTEM FOR ENVIRONMENTAL MONITORING

This application claims priority to U.S. Provisional Application Ser. No. 61/133,343, filed Jun. 27, 2008, whose entire disclosure is incorporated herein by reference.

BACKGROUND OF THE INVENTION

1. Field of the Invention

The present invention relates to monitoring of environmental parameters and, more particularly, to a wireless sensor system with sensor nodes that can be deployed over a wide monitoring area.

2. Background of the Related Art

There is a great need for distributed measurements of environmental parameters in DoD sites to meet Total Maximum Daily Load (TMDL) requirements and to gauge sources and dynamics of pollution in large water bodies.

Current sensor platforms are relatively big, e.g., floats that are several feet long, or moored buoys. The sensors that are designed for use on these platforms tend to be bulky in design.

Currently used commercial sensors are based on a variety of operational principles. For example, dissolved oxygen (DO) is usually measured using a membrane covered amperometric cell that has a current output, pH is measured with a potentiometric electrode with voltage output, and turbidity is measured using an optical transducer by transmission, reflection, or backscattering methods. Conductivity is measured by contact (current through 2 or more electrodes) or contact-less (inductive) methods. Further, $CO_2$ is rarely measured with sensors.

Many contaminants are generally measured in the laboratory using chromatography. This variety mandates the use of multiple electronic front-ends capable of handling the signal from the transducers. As a result, integration is difficult.

SUMMARY OF THE INVENTION

An object of the invention is to solve at least the above problems and/or disadvantages and to provide at least the advantages described hereinafter.

Therefore, an object of the present invention is to provide a system and method for wirelessly monitoring multiple environmental parameters, such as dissolved oxygen, pH and turbidity.

To achieve at least the above objects, in whole or in part, there is provided a wireless sensor system for monitoring at least one environmental parameter that includes a base station, and at least one sensor node in wireless communication with the base station, wherein the sensor node comprises at least one sensor for monitoring at least one environmental parameter, and a watertight and buoyant enclosure for housing electronics associated with the at least one sensor.

To achieve at least the above objects, in whole or in part, there is also provided a sensor node for monitoring at least two environmental parameters that includes at least one sensor for monitoring at least one environmental parameter, a wireless communication system for wirelessly transmitting data from the at least one sensor, and a watertight and buoyant enclosure for housing electronics associated with the at least one sensor and the wireless communication system.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

BRIEF DESCRIPTION OF THE DRAWINGS

The invention will be described in detail with reference to the following drawings in which like reference numerals refer to like elements wherein:

FIG. 19 is a table showing one possible implementation for the codes for the different light sources and detectors in the wireless sensor system of the present invention.

DETAILED DESCRIPTION OF PREFERRED EMBODIMENTS

The present invention provides a wireless sensor system that utilizes reliable, small, inexpensive and low power-consuming sensor nodes for monitoring environmental parameters that can communicate through wireless transmitters to a base station. The sensor nodes preferably incorporate anti-biofouling protection, so as to withstand continuous field deployment in streams and/or riparian areas.

Figure 1:
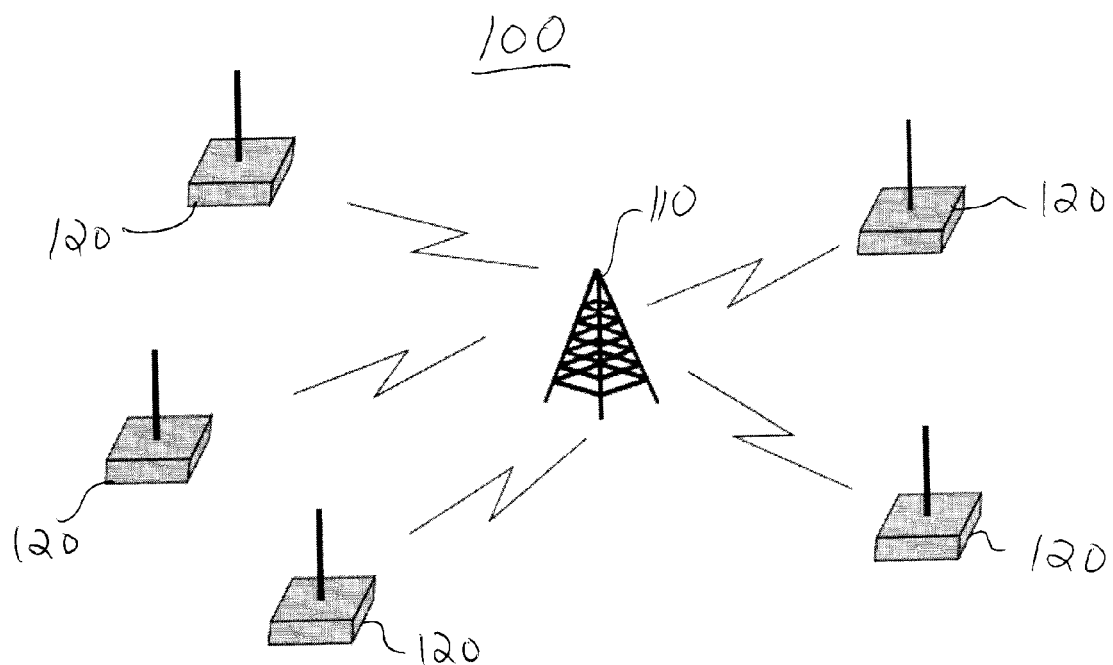
FIG. 1 is a schematic diagram of a wireless sensor system for monitoring multiple environmental parameters, in accordance with the present invention.

FIG. 1 is a schematic diagram of a wireless sensor system 100 for monitoring multiple environmental parameters, in accordance with the present invention. The system 100 includes a base station 110 and wireless sensor nodes 120 that are distributed over an observation area for measurement for multiple environmental parameters. The base station 110 and sensor nodes 120 form a network that preferably incorporates a star-type structure in which one sensor node 120 is queried at a time.

Each sensor node 120 preferably includes sensors for measuring multiple environmental parameters. In one preferred embodiment, each sensor node 120 includes a pH sensor 130, a dissolved oxygen (DO) sensor 140 and a turbidity, or optical density (OD), sensor 150, as shown in the schematic diagram of FIG. 2. The sensors 130, 140, 150 are preferably powered by batteries housed in a battery holder (not shown).

The sensor node 120 preferably consists of five functional blocks: (1) a light source system that includes light sources 160a, 160b and 160c, and voltage controlled current sources 165; (2) a detection block that consists of detection systems 170a, 170b and 170c; (3) a lock-in detection block that consists of frequency generator 210, synchronous rectifier (multiplier) 200 and low-pass filter 190; (4) a control block that consists of a microcontroller 230 and A/D converter 240; and (5) a radio-frequency (RF) block that consists of transmitter 220.

Every functional block described above preferably has its own power supply regulator (not shown). This allows each respective functional block to power down if not in use. Furthermore, the voltage requirements in the sensing/detection path are different—the amplifiers 250a, 250b and 250c and the microcontroller 230 preferably operate at 3.3 V, while 4.75 V is preferably used to drive the LEDs 260a, 260b, 260c and 260d. The RF block (transmitter 220) preferably has its own power supply (not shown), which is additionally filtered for better suppression of spurious pulses resulting from the amplification of the RF noise.

Light Source Block

The excitation light is preferably generated by LEDs. In the embodiment shown in FIG. 2, three types of LEDs are preferably used: a blue LED (an emission maximum of preferably approx. 460 nm), a violet LED (an emission maximum of preferably approx. 400 nm) and an orange LED (an emission maximum of preferably approx. 600 nm). The pH sensor 130 preferably uses a blue LED 260a and a violet LED 260b. The LED 260c in the oxygen detector 140 is preferably either a blue LED or an orange LED. The turbidity (OD) sensor 150 preferably uses an orange LED 260d.

Excitation filters 320a and 320b are preferably used in the pH sensor 130 and oxygen sensor 140, respectively. The filters 320a and 320b are positioned in front of the excitation LEDs, and preferably pass wavelengths between 400 nm and 480 nm, and absorb wavelengths outside that range. The filters 320a and 320b are preferably made of Schott glass (BD12), which exhibits a desirable property that the cut-off wavelength does not depend on the incidence angle of the light.

Light from the LEDs is preferably modulated at predetermined frequency in order to distinguish the LED light from ambient light. Furthermore, the light intensity during the peak is preferably constant to ensure proper fluorophore excitation. This is preferably achieved by the use of voltage controlled current sources (VCCS) 165 based on common op-amp topology.

The LEDs 260a, 260b, 260c, 260d are preferably operated as a floating load. The use of high frequency video amplifiers in the VCCS 165 achieves modulation frequencies up to 10 MHz. The light can be suitably modulated at 10 kHz for the pH sensor 130 and OD sensor 150, and at 130 kHz for the oxygen sensor 140.

Detection Block

Photodetectors 270a, 270b and 270c are used in pH sensor 130, oxygen sensor 140 and OD sensor 150, respectively. Photodetector 270a is used to measure the changes in the optical properties of pH sensor patch 280, photodetector 270b is used to measure changes in the optical properties of oxygen sensor patch 290 and photodetector 270c is used to measure light coming from OD optical sensor 300. The operation of the pH sensor patch 280, the oxygen sensor patch 290 and the OD optical sensor 300 will be explained in more detail below.

PIN photodiodes are preferably used for the photodetectors 270a, 270b and 270c, with large surfaces (preferably 7 mm$^2$) and a low capacitance (preferably 25 pF or less at a reverse bias voltage of 2.5 V). As the photodiodes produce current proportional to the intensity of the light, differential transimpedance amplifiers (TAs) 250a, 250b and 250c are preferably used to convert the outputs of the photodiodes into voltage. The use of differential input ensures high common mode rejection ratio, which is important for detection of current on the order of several pA. The signal is preferably amplified ~100 times in the subsequent stages. In order to avoid simultaneous amplification of the offset voltages, DC currents, and low frequency noise, the stages are preferably separated using high-pass filters (not shown).

Emission optical filters 330a, 330b and 330c are preferably used in front of the photodetectors 270a, 270b and 270c, respectively. The emission filter 330a in the pH sensor 130 is preferably a band-pass filter that passes wavelengths of 550 nm±20 nm. The emission filter 330b in the oxygen sensor 140 is preferably a long-pass filter with a 600 nm cut-off wavelength. The emission filter 330c in the turbidity (OD) sensor 150 is preferably a red filter with a transmission maximum at a wavelength of 620 nm.

Lock-In Detection Block

Modulating the light from the LEDs electronically allows the use of a lock-in detection approach for detection of fluorescence. The lock-in detection approach allows determination of the amplitude and the phase of the received signal.

Immediately after amplification stages, a synchronous rectifier 200 is used and is preferably driven with the excitation frequency shifted at 0° and 90° out of phase. In essence, it operates as a square wave mixer multiplying the incoming signal A sin(ωt+φ)) with the in-phase sin(ωt) and quadrature sin(ωt+90) of the excitation signal:

$$IP(t)=A\sin(\omega t+\phi)\cdot\sin(\omega t)=A2(\cos(2\omega t+\phi)+\cos(\phi)) \quad (1)$$

$$QD(t)=A\sin(\omega t+\phi)\cdot\sin(\omega t+90)=A\sin(\omega t+\phi)\cdot\cos(\omega t)$$
$$=A2(\sin(2\omega t+\phi)+\sin(\phi)) \quad (2)$$

After rectification, the signal is preferably averaged using low-pass filter 190. This operation is equivalent to the removal of the high-frequency components in equations (1) and (2). Hence, after the low-pass filter 190, only low frequency and DC values are obtained. Their ratio, QD/IP is equal to the tangent of the phase difference between excitation and the emission fluorescence signal. Similarly, QD2+ IP2 is equal to the amplitude of the measured signal.

For the pH sensor 130, the operational principle requires the detection of two amplitudes (the emission when the sensor is illuminated at two different wavelengths) to find their ratio. The ratio removes the measurement inaccuracies related to the variation of the light path length, positioning of the sensing patch 280, and attenuation of the light in the illumination path.

Figure 3:
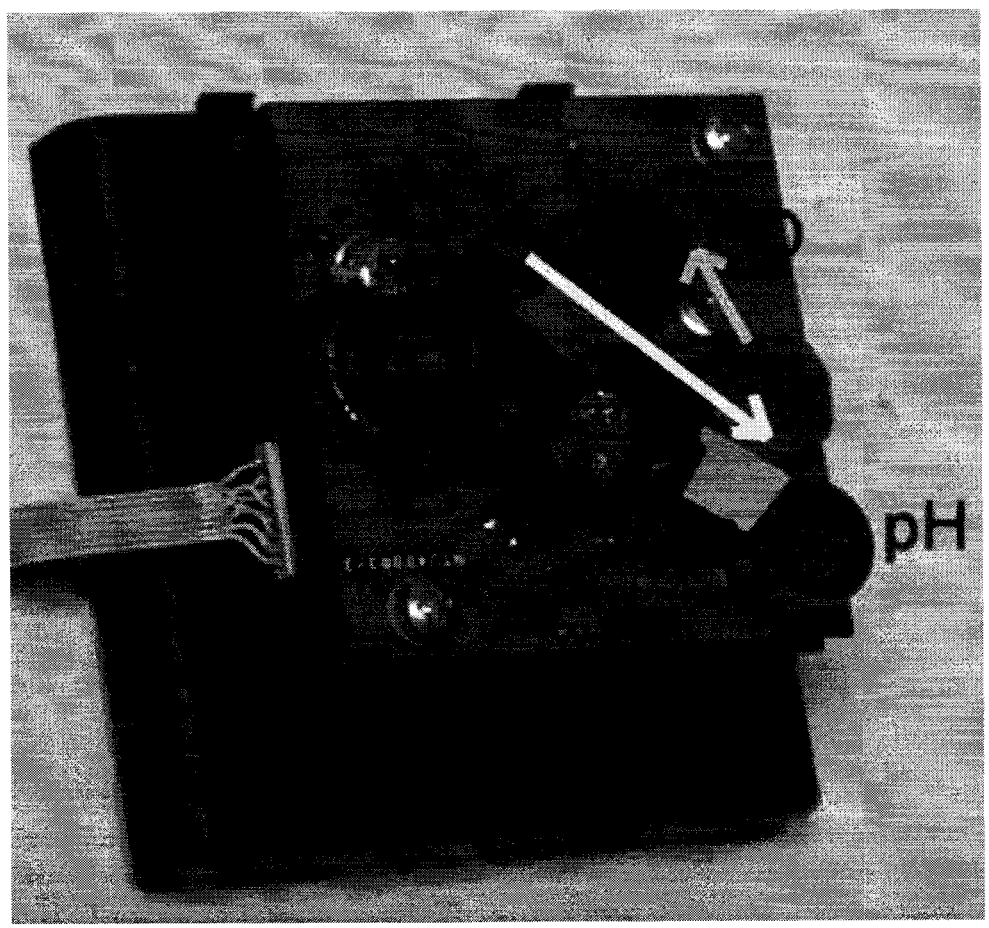
FIG. 3 is a perspective view of a detection block used in the sensor node of FIG. 2, in accordance with one embodiment of the present invention.

For the oxygen sensor 140, the phase shift generated by illumination of the patch with orange and blue light is detected. The orange light is simulating the fluorescence of the patch with zero phase shift. The orange light is used to account for the phase delays introduced by the electronics. At the operational frequency (preferably 130 kHz), the phase shift is significant)(~43°). It is known that the phase shift depends on the ambient temperature. The difference between the phases measured with the use of the blue and the red illumination gives the actual phase shift of the sensor. Measurements of phase shift have the same advantages as the measurements of the spectral ratios. A perspective view of the detection block is shown in FIG. 3, with the arrows showing the spatial direction of the light emissions.

Control Block

An on-board microcontroller 230 is preferably used to perform the calculations required for the measurements. The microcontroller 230 is preferably a low cost, medium complexity system-on-chip. The core is suitably built around a very-low-power microcontroller with built-in 16 bit A/D converter and 1.2 V voltage reference. It preferably has on-chip flash memory and random access memory (RAM), as well as arithmetic registers. The microcontroller 230 preferably has 2 digital ports, that are used to control which part of the node is operational (RF part or sensor part). Additionally, the microcontroller 230 addresses the respective measurement channel (OD, pH, or oxygen) and measures the values. It also performs the wireless communication, preferably using a software based universal asynchronous receiver/transmitter (DART).

RF Block

The communication between the sensor node 120 and the base station 110 is performed using transmitter 220 and a corresponding receiver on the base station 110, which will be shown and described below. The transmitter 220 and receiver preferably operate at a frequency of 433 MHz, but any other communications frequency can be used. A frequency of 433 MHz is preferred because it is license free (ISM band), and because it penetrates through concrete fairly easily.

The RF block preferably operates in OOK protocol (on-off keying), where the presence of a signal is considered logical 1 and the absence of a signal is considered logical 0. While this protocol has maximum transmission rate limitation of 10 kbaud, it is advantageous from the point of view of power conservation. In one preferred embodiment, a transmission rate of 2.4 kbaud is used.

Figure 2:
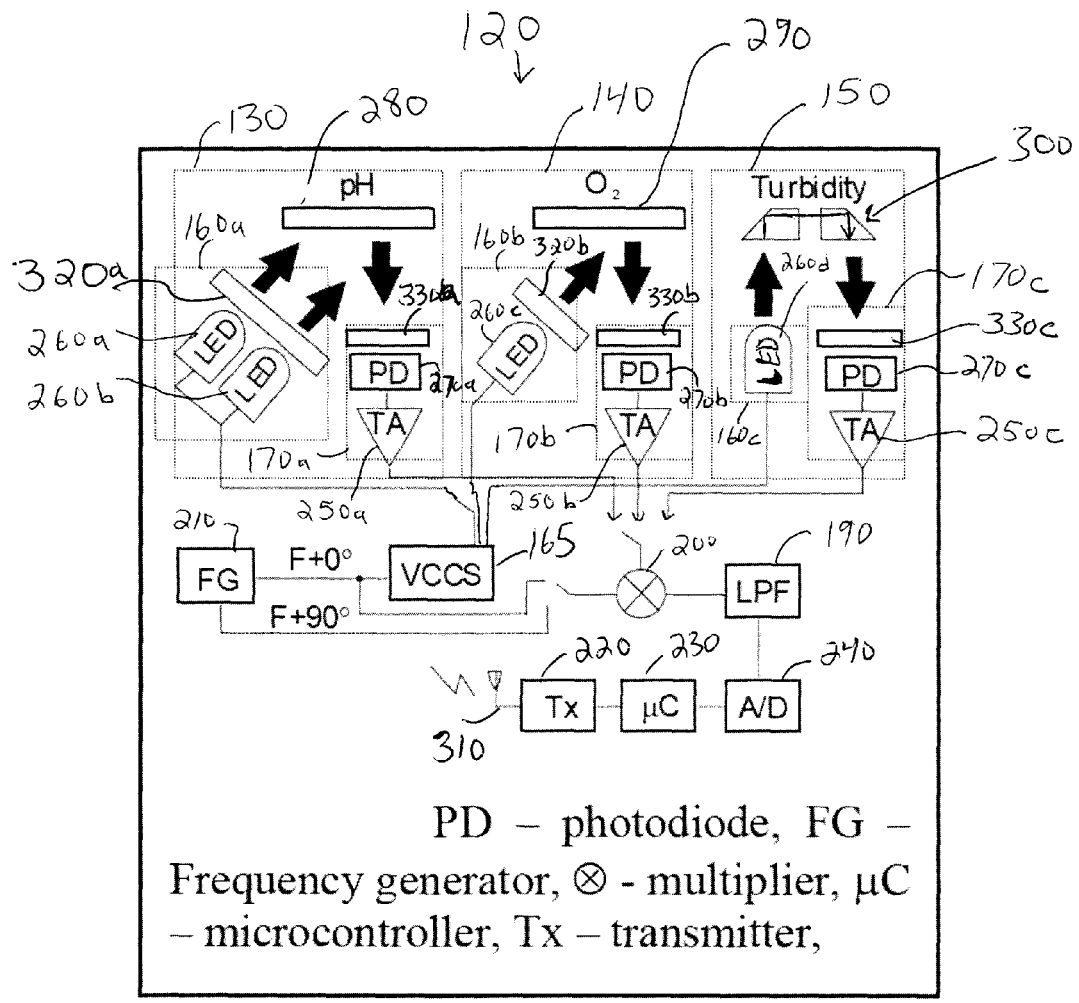
FIG. 2 is a schematic diagram of a sensor node used in the wireless sensor system of FIG. 1, in accordance with one embodiment of the present invention.
Figure 4:
FIG. 4 is a perspective view of control and RF blocks used in the sensor node of FIG. 2, in accordance with one embodiment of the present invention.

FIG. 4 is a perspective view of the control and RF blocks. As shown in FIGS. 2 and 4, an antenna 310, preferably a quarter-wave whip antenna, is used to transmit signals to and receive signals from the base station 110. A quarter-wave whip antenna provides a circular emission diagram and an omnidirectional communication capability. Further, use of this type of antenna allows it to be mechanically positioned in the center of gravity of the sensing node 120, which the sensor node 120 less prone to being overturned.

Figure 5:
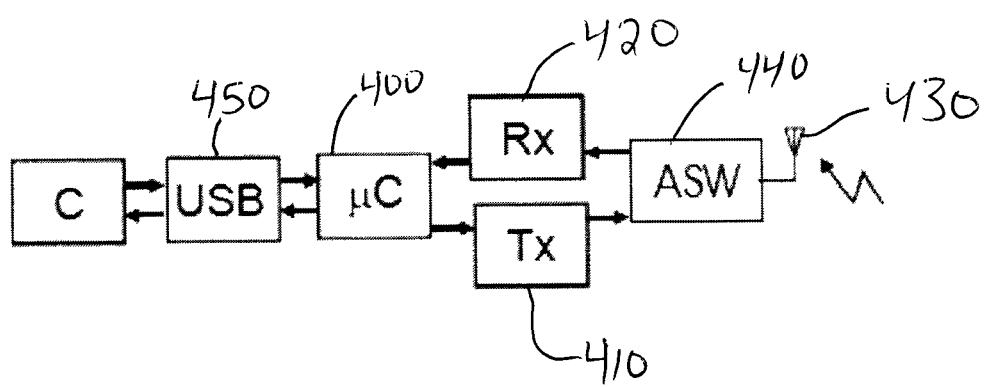
FIG. 5 is a schematic diagram of the electronics used in the base station of FIG. 1, in accordance with one embodiment of the present invention.

FIG. 5 is a schematic diagram of the electronics for the base station 110. It is simpler than the schematics for the sensor node 120, because it only performs communication functions. The base station 110 preferably consists of a microcontroller 400, which handles the data traffic, a transmitter module 410 and a receiver module 420 connected to an antenna 430 through an antenna switch 440, and a USB controller 450.

The microcontroller 400 preferably has two independent ports, and monitors the pins, controls the data direction to the transmitter and receiver modules 410, 420 and respectively switches the antenna switch 440 to enable effective wireless traffic.

pH Sensor Patch

Optical pH detection is based on indicator dyes. A successful example is a pH sensor patch based on an excitation ratiometric fluorescent dye. As such, 8-hydroxypyrene-1,3,6-trisulfonic acid trisodium salt (HPTS) is preferably used for the pH sensor patch 280. HPTS exhibits very high photochemical stability and can be polled at two excitation wavelengths that correspond to the protonated and deprotonated form. It is suitable for ratiometric measurements, which is another method for elimination of the inherent drawbacks of intensity-based measurements. Excitation maxima are at 405 and 455 nm, which allows excitation by ultraviolet (UV) and blue LEDs.

The ratiometric determination using excitation ratiometry of a fluorescent dye is described by the following relationship:

$$R = \frac{I_{\lambda_1} \cdot \phi_{\lambda_1} \cdot \varepsilon_{\lambda_1} \cdot [Ind^-]}{I_{\lambda_2} \cdot \phi_{\lambda_2} \cdot \varepsilon_{\lambda_2} \cdot [H-Ind]} \qquad (3)$$

Here, $I_{\lambda_1}$ and $I_{\lambda_2}$ the light intensities at excitation wavelengths $\lambda_1$ and $\lambda_2$, $\phi_1$ and $\phi_2$ are the quantum yields of the luminophore at these wavelengths, $\varepsilon_1$ and $\varepsilon_2$ are the respective molar absorptivities, [H-Ind] is the concentration of undissociated dye, and [Ind$^-$] is the concentration of the dissociated dye. Recalling that [H-Ind]+[Ind$^-$]=[T], where [T] is the total amount of the indicator in the sensor (it is known and constant due to immobilization), it is easy to establish the calibration function of the sensor.

Figure 6:
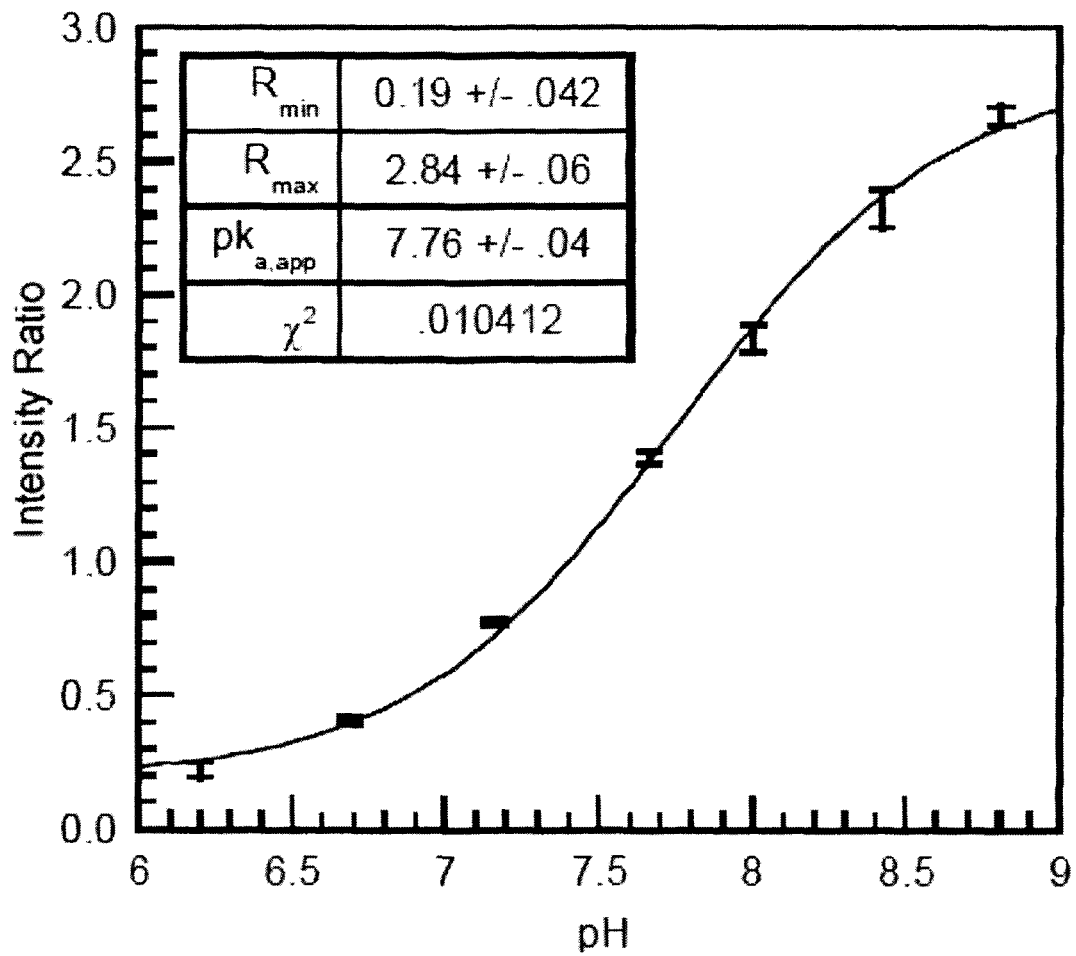
FIG. 6 is a graph of a typical transfer function of a pH sensor.

A typical transfer function of a pH sensor is shown in FIG. 6. The dye is covalently immobilized in a hydrophilic matrix (polyethylene glycol diacrylate). The matrix ensures rapid penetration of the hydrogen ions while successfully preventing the dye from leaching. The polyethylene glycol membrane also provides biofouling protection.

The pH sensor patch 280 is preferably synthesized in accordance with the procedures set forth in U.S. Pat. Nos. 7,029,630 and 7,390,462, which are incorporated by reference herein in their entirety. Briefly, the indicator dihydroxydisulphonic acid (100 mg) is dissolved in dimethyl formamide (10 mL) in a 25 mL reaction vessel. Potassium carbonate (1 g) and methacrylic anhydride (1:1 eq., 36 mL) are added. The vessel is then closed with a stopper and placed in a 70° C. water bath to react for 12 h.

Then, the cooled reaction mixture is filtered. The solvent is removed from the filtrate in a rotary evaporator to yield the crude solid product hydroxypyrene disulfonic acid methacrylate (MAHPDS). Next, a silicone layer attached to the top of a polyester foil is prepared to be chemically bonded with the sensing polymeric matrix layer. The activation was performed in two steps: a) oxidation of the silicone and b) creation of an intermediate monolayer between the silicone rubber and the future polymeric hydrogel layer. Oxidation is performed in oxygen plasma, at 150 mTorr oxygen pressure, and 100 mW power.

Immediately after oxidation the silicone-polyester foil is immersed in DI water for 5 minutes. The foil is then dried in a vacuum. The intermediate layer is prepared with a methacrylic group reacting trimethoxysilane monolayer. One ml glacial acetic acid is dissolved in 10 ml deionized water, and 200 μl [3-(Methacryloyloxy)propyl] trimethoxysilane is dissolved in 20 ml absolute ethanol. 600 μl of the first glacial acetic acid solution was added to the ethanol solution just prior to use.

The surface of the oxidized and dried silicon rubber is treated with this mixture for 5 minutes, then washed 3 times with absolute ethanol and dried. Finally, the derivatized dye MA-HPDS was crosslinked over the silicone.

A stock solution of MA-HPDS in deionized water (10 mg/mL) is prepared. Polymer precursor solution is prepared by combining 45 mg of PEG-DA, 200 mL of deionized water, 100 mL of the MAHPDS stock solution and 6 mL of the photoinitiator Darocur and vortexing for 30 min. The solution is spread on the treated silicone and covered with filter paper to provide optical shielding. The solution is polymerized between glass plates to prevent oxygen inhibition and volume contraction of the gel. Free radical polymerization of the acrylate end groups is initiated by exposure to a 100 W long wave UV spot lamp for 4 min.

Figure 7:
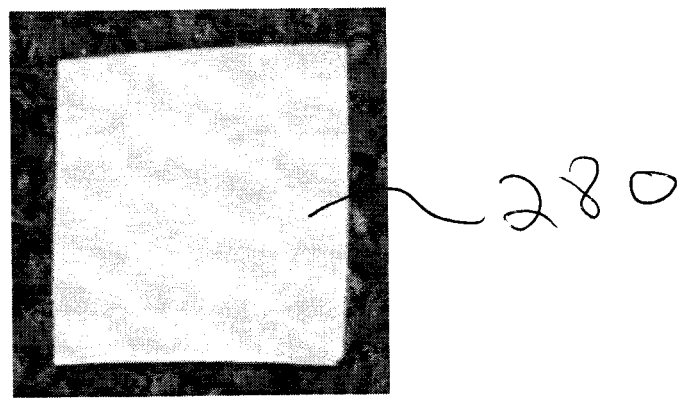
FIG. 7 is a perspective view of pH sensor patch used in the sensor node of FIG. 2, in accordance with one embodiment of the present invention.

After polymerization, the foils are washed in deionized water for at least 48 h with several changes of the wash solution. This step serves to both hydrate the matrix and to remove any unbound dye. The resulting pH sensor patch 280 is shown in FIG. 7.

Figure 8:
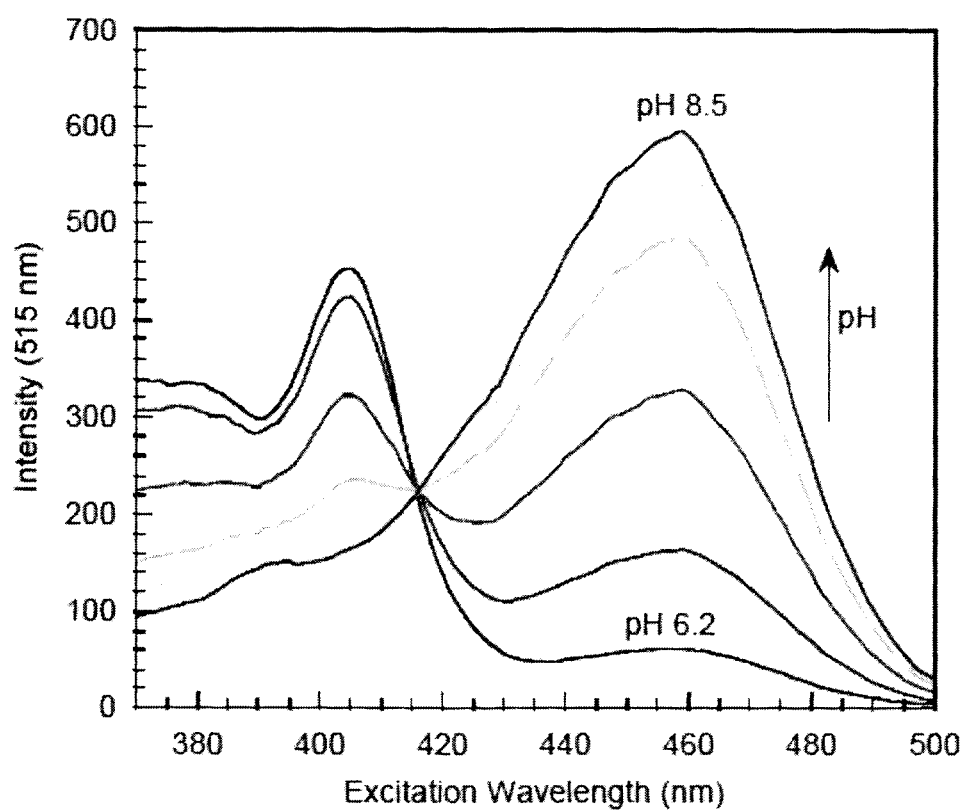
FIG. 8 is a graph of the excitation spectra of the pH sensor patch used in the sensor node of FIG. 2, in accordance with one embodiment of the present invention.

The pH sensor patch 280 is preferably characterized using a steady state fluorometer. The titration of the sensor patch 280 with buffers with various pH shows the two excitation peaks of the dye positioned at 410 nm and 460 nm, as shown in the graphs of FIG. 8. As the dye fluorescence decay rate is approximately 5 ns, the excitation light can be measured with steady-state excitation. It can be also modulated with practically any frequency below 1 MHz without changes in the amplitude of the fluorescence. Modulation helps to discriminate between the fluorescence and the ambient light, as the sensor patch 280 has to operate in the field.

Oxygen Sensor Patch

Optical detection of oxygen partial pressure ($pO_2$) is based on quenching of emission of a fluorescent metal-ligand complex as described previously (Szmacinski and Lakowicz, 1994; Tolosa, et al., 2002). Briefly, the excited state of the luminescent dye (i.e. tris(diphenylbipyridine) ruthenium chloride) is collisionally quenched proportionately to the oxygen concentrations, resulting in a change in the emission intensity F and the fluorescence lifetime τ. This process is described by the Stern-Volmer equation, $$\frac{F_0}{F} = \frac{\tau_0}{\tau} = 1 + K_{SV} \cdot [O_2] \quad (4)$$

where $\tau_0$ and $F_0$ are the decay time and intensity in the absence of oxygen, respectively, $K_{SV}$ is the Stern-Volmer constant and $[O_2]$ is the oxygen concentration.

Figure 9:
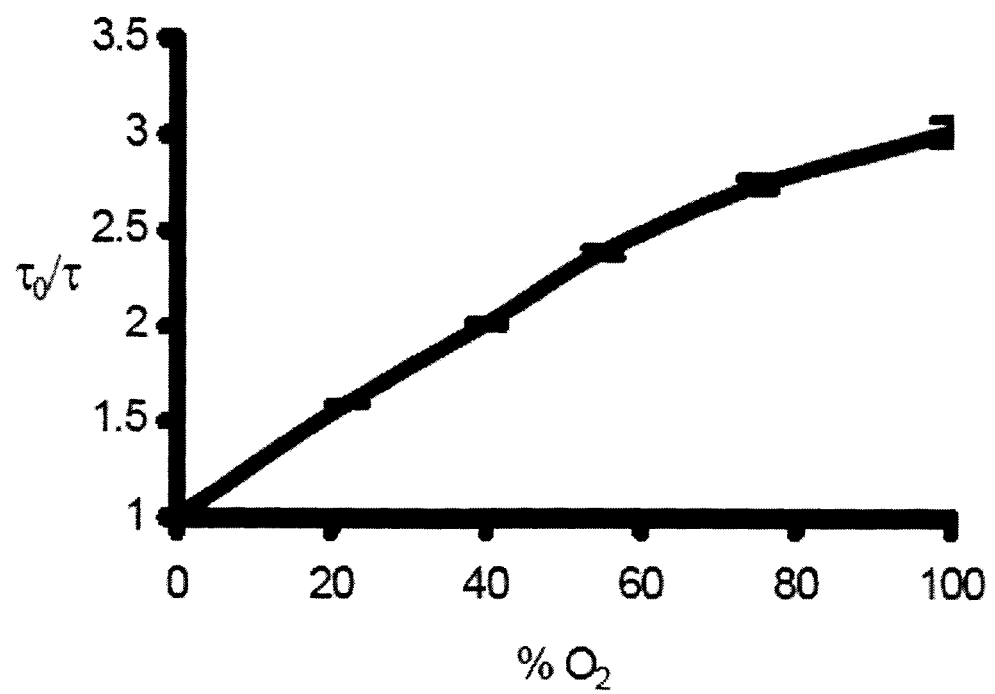
FIG. 9 is a graph of a typical transfer function of an oxygen sensor.

A typical transfer function of an optical oxygen sensor patch is shown in FIG. 9. The intensity measurements are unreliable due to photodecomposition, instability of the source or detector, scattering or even minor optical changes in the optical path. For this reason, lifetime detection is the preferred technique. Fluorescence lifetime in the absence of oxygen is an intrinsic property, and serves as an internal reference. Furthermore, as this is an equilibrium process, neither the analyte, nor the dye is consumed. Consequently, this method has found a place in high-reliability, low power applications.

For sensing, the dye is immobilized in a membrane, which prevents the interaction of the dye with aqueous species. This is achieved by entrapping the dye on the surface of preferably, 5 μm diameter particles of ion-exchange resin, which is subsequently dispersed in a layer of silicone rubber. The resin-bound dye stays in ionized form, which prevents it from recrystallizing.

Dye crystals are not oxygen sensitive, and the resin binding significantly enhances the long-term stability of the oxygen sensor patch 290. The encapsulation in silicone rubber, which is hydrophobic, prevents the interaction of the dye with the ionic species in water. It does not interfere with the oxygen transfer because of the extremely high solubility of oxygen in the rubber. Another attractive feature is the availability of simple technology for covalent attachment of polyethyleneglycol (PEG) layers, which would serve as protection from biofouling.

In portable instrumentation, a method of choice for the dye's lifetime determination is frequency domain fluorometry. There, lifetime is measured by illuminating the sensing patch with intensity modulated light at a frequency $\omega$ ($\omega=2\pi f\times$ Hz) generated from a light emitting diode (LED) and measuring the phase shift φ of the resulting emission. The relationship between the lifetime and the phase shift is given by $\tan \phi = \omega \cdot \tau$.

As discussed above, optical oxygen sensing relies on the use of dyes with a fluorescence decay rate (DR), in the absence of oxygen, in the range 100 ns–10 μs. Ruthenium polypyridyl complexes are used most often because of their high quantum yield (QY) and resistance to photobleaching. Of these, the most widely used is Ru tris (diphenylphenanthroline) dichloride, which is a commercially available dye with QY~0.4 and DR~5 μs. However, the literature data suggest that the dye is not quite suitable for long-term measurements (months).

For long-term stability, the use of a dye without the phenanthroline bridge is preferred. One dye that satisfies this requirement is Ru tris (diphenylbipyridine) dichloride (RuDPBP), which has QY~0.2 and DR~1 μs. Because this dye is not available commercially, it is preferably synthesized according to a procedure set forth in Kosch et al., Strategies to Design pH Optodes with Luminescence Decay Times in the Microsecond Time Regime, *Anal. Chem.* 70, 3892-3897 (1998), which is incorporated by reference herein in its entirety.

Briefly, 225 mg RuCl and 800 mg of 4,4'-diphenyl-2,2'-bipyridyl is dissolved in 10 mL acetone, 5 mL of ethylene glycol and 0.2 mL of water and heated under constant stirring until the acetone evaporates. Then, the dark violet solution is refluxed for another 60 minutes. The color of the solution turns from violet to red-dark brown.

After the solution is cooled to room temperature, 50 mL of acetone is added. Ten milliliters of this solution is treated with 50 mL of a 1 M solution of NaCl, upon which a dark-red precipitate is formed. It is filtered and washed with 20 mL of water and 40 mL of ether. The compound is additionally purified using alumina column chromatography.

The oxygen sensor patch 290 is prepared by first immobilizing the dye electrostatically on silica gel. One gram of Davisil, grade 710 is then stirred for 15 minutes in 20 mL 0.01 N NaOH. A solution of 20 mg RuDPBP in 5 mL ethanol is then slowly added, and the mixture is stirred for 20 min. The resulting deeply colored particles are filtered out, washed three times with 50 mL deionized water, and dried in a vacuum.

Figure 10:
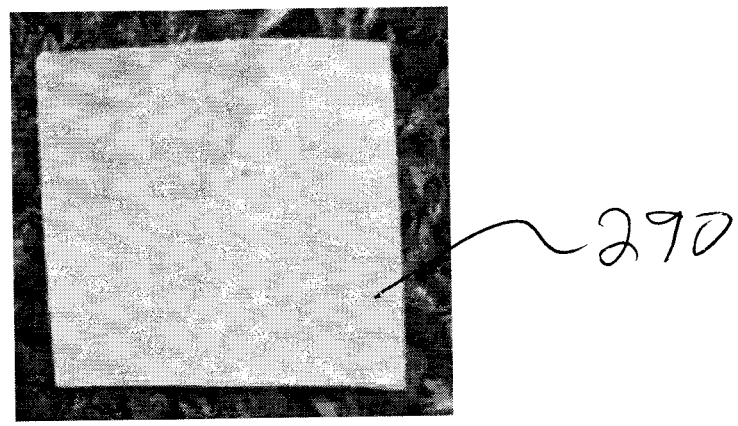
FIG. 10 is a perspective view of an oxygen sensor patch used in the sensor node of FIG. 2, in accordance with one embodiment of the present invention.

One gram of silicon RTV sealant 732 is then dissolved in 5 mL toluene. Two hundred milligrams of the dyed particles are added and the solution is stirred for 6 hours. The resulting suspension is spread on a polyester sheet, preferably 0.2 mm, and covered with a hydrophobic filtering membrane. The resulting sandwich is left to dry for 24 hours, and a water-stable, pressure sensitive adhesive is attached on the polyester sheet. The resulting patches are cut in squares (0.75"×0.75") and used as peel-and-stick oxygen sensor patches 290 for use in the oxygen sensor 140. The resulting oxygen sensor patch 290 is shown in FIG. 10.

Figure 11:
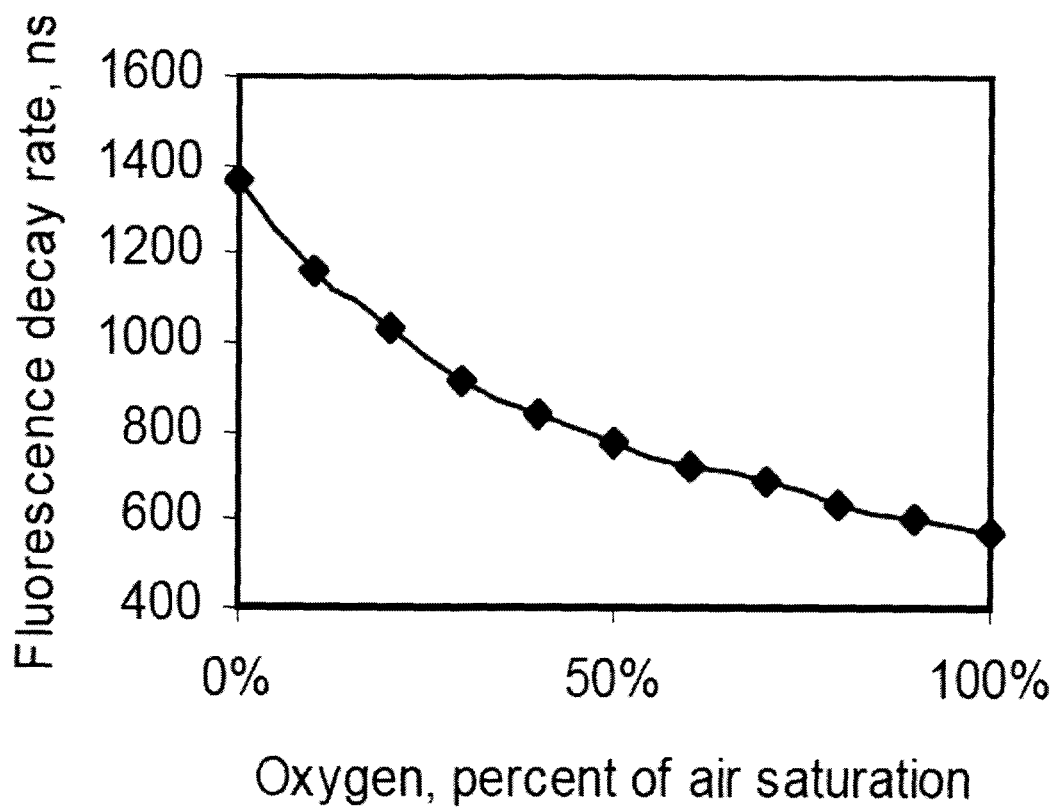
FIG. 11 is a graph of fluorescence decay rate as a function of oxygen concentration for the oxygen sensor patch used in the sensor node of FIG. 2, in accordance with one embodiment of the present invention.

The prepared oxygen sensor patches 290 were characterized with respect to the fluorescence decay rate as a function of the oxygen concentration. The oxygen patches 290 were measured using frequency-domain lifetime fluorometer ISS Koala (ISS), and the results are shown in the graph of FIG. 11. The lifetime of the fluorescence steadily decreases from approximately 1.4 μs in nitrogen to around 600 ns in air. This result suggests that the oxygen can be easily determined using frequency domain fluorometry. However, it is necessary to determine the optimum frequency for the excitation light.

Figure 12:
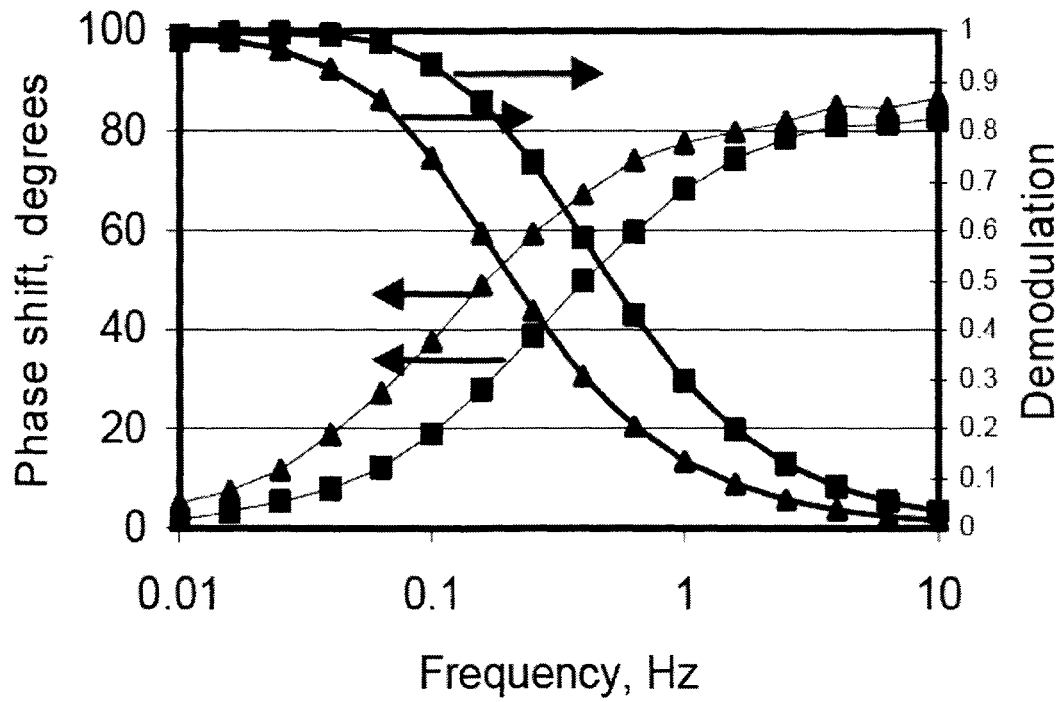
FIG. 12 is a graph of phase shift and the modulation plots at different modulation frequencies in air and $N_2$ for the oxygen sensor patch used in the sensor node of FIG. 2, in accordance with one embodiment of the present invention.

For this reason, the phase shift and the modulation plots at different modulation frequencies in air and $N_2$ were examined, and are shown in FIG. 12. The maximum difference between the phase shifts is achieved when the excitation light is modulated in frequency range 100-250 kHz. A closer investigation (results not shown) determined the optimum frequency as 130 KHz. This was the minimum frequency at which the phase shift difference between air and $N_2$ were greatest (23° C.). This phase difference is the range of the oxygen sensor patch output when the input changes between 0 and 100% of air saturation. Further increase of the frequency brought only a marginal increase in the range (<1), at the price of a significant increase in the modulation frequency, which would result in worse output noise and more complex electronics.

When excited with blue light (460±15 nm), the oxygen sensor patch 290 emits red light with an emission maximum at 630 nm±15 nm. When the excitation light is modulated at 130 kHz, the resulting signal is ~24° in air and ~46° in nitrogen. It was found also that the phase shifts are sensitive to temperature, ~2%/° C., requiring temperature compensation for field use.

Optical Path

In fluorescence measurements, it is typical to select an optical path in which the fluorescence detector is positioned at 90° to the direction of the excitation beam. The reason is the relatively low quantum yield of the emission and the fact that fluorescence is isotropic. As a result, the intensity of the collected light can be several orders of magnitude lower than the excitation light. Further, the wavelength selection devices (filters, monochromators) attenuate the unwanted wavelengths, but do not completely exclude it. Hence, any additional suppression of the excitation light enhances the signal to noise ratio.

From this point of view, the 90° orientation is most favorable because this is the direction of minimum Rayleigh scattering (scattering of the light by the molecules). However, this approach is not possible with fluorophores immobilized in a thin (100 μm) patch. First, it would be difficult to focus the light exactly at the patch edge. Second, because of the aspect ratio of the patch (thickness/length=1/200), the fluorophore would be excited mainly at the edges.

Figure 13:
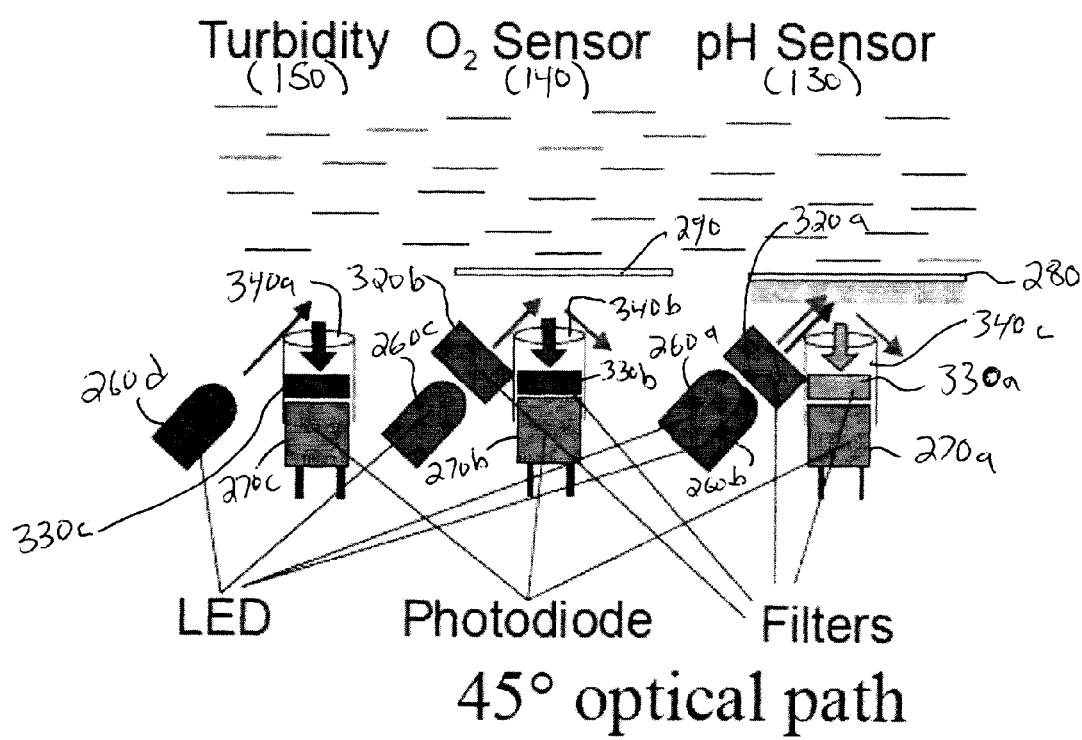
FIG. 13 a schematic diagram showing the preferred positioning of the LEDs and detectors in the pH sensor, oxygen sensor and turbidity sensor in the sensor node of FIG. 2, in accordance with one embodiment of the present invention.

For these reasons, it is preferable to position the optical axis of LEDs 260a, 260b and 260c at 45° in respect to the optical axis of the photodetectors, as shown in FIG. 13, which is a schematic diagram showing the preferred positioning of the LEDs and detectors in the pH sensor 130, oxygen sensor 140 and turbidity sensor 150. In this way, the majority of the reflected excitation light travels away from the photodetectors 270a, 270b and 270c. While the amount of the scattered light is increased, it is still within the range that can be successfully suppressed using filters. Finally, in order to restrict the directionality of the incoming light, apertures 340a, 340b and 340c are positioned in front of every photodetector.

As discussed above, because the pH sensor patch 280 requires excitation at 400 nm and 450 nm, LEDs with different emission maxima were used. However, it was found that the prolonged illumination with one of the wavelengths (400 nm) results in faster photo bleaching of the indicator dye as compared with illumination with the other wavelength (450 nm). As a result, if the two LEDs 260a and 260b illuminate two different spots on the pH sensor patch 280, the pH sensor patch 280 bleaches at different rates and the emission intensities from these spots begin to differ over time. This leads to a drift of the sensor signal.

Figure 14:
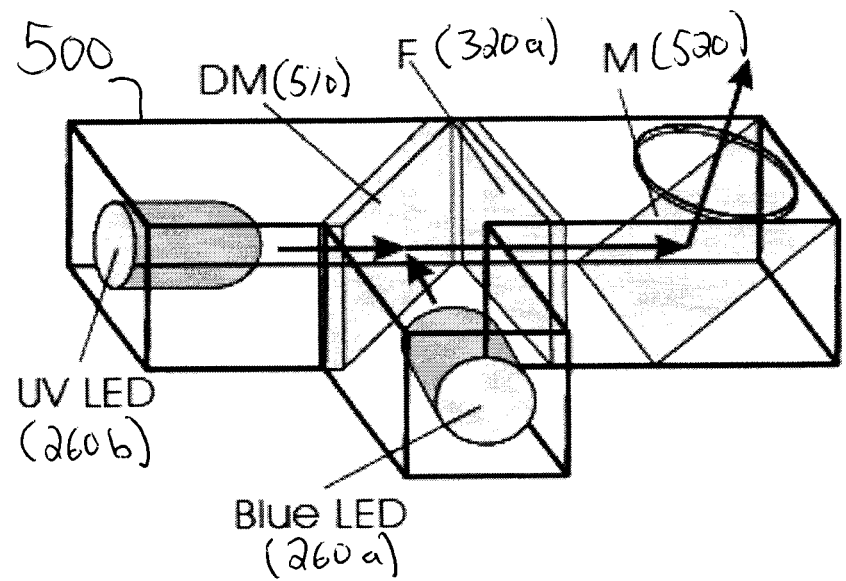
FIG. 14 is a schematic diagram of a beam combiner used in the sensor node of FIG. 2, in accordance with one embodiment of the present invention.

To avoid this, the beam combiner 500 shown in FIG. 14 is preferably used to align the beams from LEDs 260a and 260b into a single optical path. When the beam combiner 500 is used, the LEDs 260a, 260b and the filter 320a are positioned in the beam combiner 500 as shown in FIG. 14.

The beam combiner 500 preferably uses a dichroic mirror 510 with a cutoff of wavelength of 425 nm. Below this wavelength, it transmits light. However, it reflects light in the wavelength range of 425 nm-525 nm. The dichroic mirror 510 is preferably mounted at 45° to both LEDs 260a, 260b, the excitation filter 320a is preferably mounted perpendicular to the combined optical beam, and a mirror 520 is preferably positioned at an angle of 30° to the plane of the LEDs 260a, 260b. The mirror 520 ensures the 45° incidence angle with the pH sensor patch 280 discussed above. The back ends of the LEDs 260a, 260b are preferably covered with black optical insulator (not shown) to avoid light leakage.

Enclosure and Mechanics

The mechanics of the sensor node 120 are preferably designed to optimize: (a) the positioning of the optoelectronics in their respective environments; (b) protection of the electronics from shocks, water and moisture; and (c) the floatability of the sensor node 120.

Figure 15:
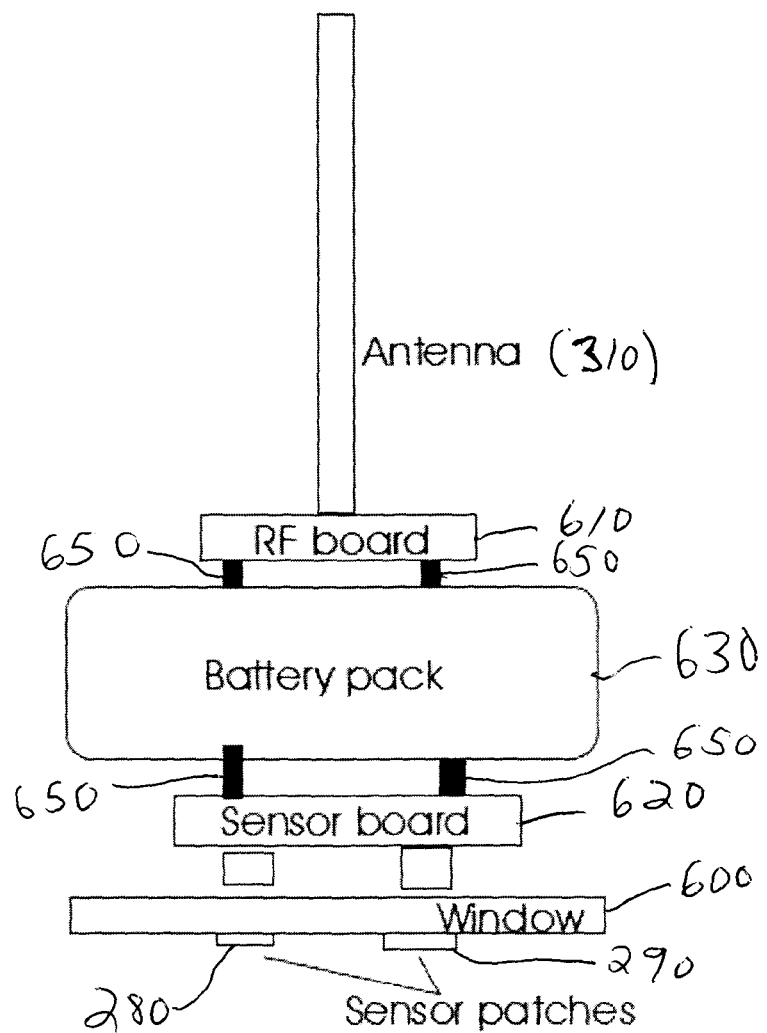
FIG. 15 is a schematic diagram showing the mechanical positioning of the components of the sensor node of FIG. 2, in accordance with one embodiment of the present invention.

FIG. 15 is a schematic diagram showing the mechanical positioning of the components of the sensor node 120. The sensor patches 280, 290 are attached to an observation window 600, both of which will be submerged in the water. However, in order to ensure a relatively long transmission range, the antenna 310 has to be outside of the water.

One goal is for the sensor node 120 to be compact. Thus, the electronics boards 610 and 620 are preferably attached to a battery pack 630, that provides the power to the electronics boards 610 and 620, so the top side of the battery pack 630 supports the electronics board 610 that contains the transmitter 220, microcontroller 230 and the antenna 310. The electronics board 620 contains all of the sensing electronics and is attached to the underside of the battery pack 630. Because the battery pack 630 is the heaviest construction element, it preferably serves as a carrier for all the other elements attached using posts 650.

The sensor node 120 is housed within an enclosure that keeps the sensor node 120 afloat while keeping the observation window 600 submerged in the water. The size is preferably chosen to have the gravity and the water displacement forces balanced when the floater is submerged to approximately one half of its height.

Figure 16:
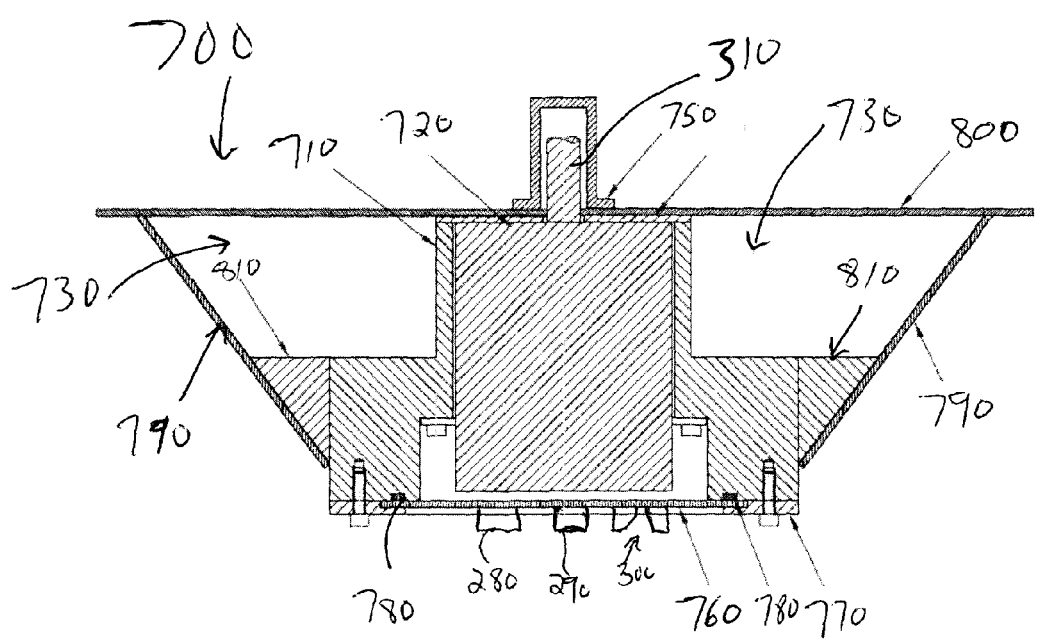
FIG. 16 is a schematic cross-sectional view of one preferred embodiment of an enclosure for the sensor node of FIG. 2.
Figure 17:
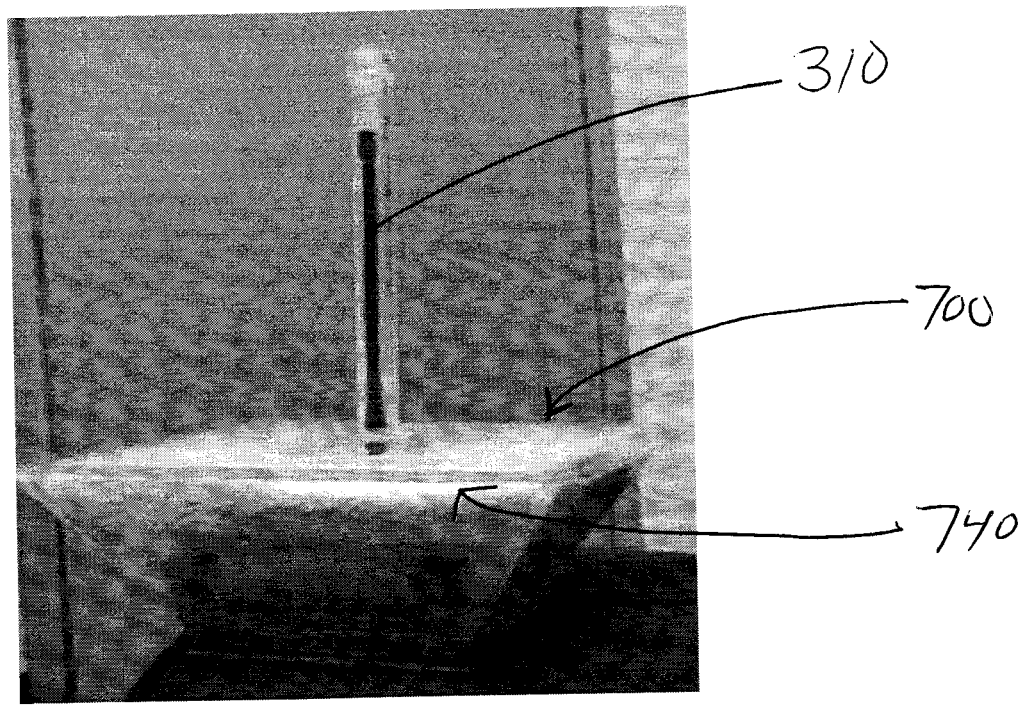
FIG. 17 is a side perspective view of one preferred embodiment of an enclosure for the sensor node of FIG. 2.

FIG. 16 is a schematic cross-sectional view and FIG. 17 is a side perspective view of one preferred embodiment of the enclosure 700 for the sensor node 120. To enhance stability in water, the cross-section of the enclosure 700 is preferably trapezoidal. With this shape, tilting to one side produces a rapidly growing displacement of water, which pushes the enclosure 700 back to the upright position. The dimensions of the enclosure 700 is preferably approximately 5 times wider than the battery pack, which increases the stability of the enclosure 700 and decreases the probability for turn-over. In the case of a turn-over, the center of gravity of the enclosure 700 is out of the water, and thus even a small disturbance will flip it back into the upright position.

The enclosure 700 is designed to have two cavities. A first cavity 710 holds the electronics 720 in place and protects them from shocks. A second cavity 730 which is filled with a buoyant material, preferably styrofoam 740 (see FIG. 17), to ensure floatation of the enclosure 700. The Styrofoam 740 is preferably added as a backup floatation medium in case a crack develops in the enclosure 700.

The first cavity 710 features a circular opening through which the antenna 310 projects out. The antenna 310 is also insulated from the environment with a plastic tube 750.

One of the most important parts of the enclosure 700 is the optical observation window 760. It is preferably made out of UVA-transparent plastic in order to allow the 395 nm excitation light for the pH sensor patch 280 to pass through. This excludes the use of polycarbonate, which would otherwise be an excellent choice because of its superior mechanical characteristics.

In one embodiment, the optical observation window 760 is manufactured out of a 0.25" acrylic polymer. However, glass or cyclic polyolefin are also preferable materials for the optical observation window 760 because of their excellent environmental stability, high transparency to UV light and minimum penetration of water vapor. The window is preferably secured in place by a metal holder 770 with a rubber gasket or O-ring 780. The water proofing of the gasket 780 is provided by application of silicon grease.

The optical observation window 760 is preferably circular shaped, which allows for easy positioning without misalignment. The sensor patches 280, 290 are attached to the observation window 760 preferably using either pressure-sensitive adhesive or silicone grease. The OD optical sensor 300 is attached to the observation window 760 preferably using optically clear cement. The rest of the enclosure 700 is made up of side sheets 790, a top sheet 800 and side sheet support 810.

Software

The software support for the wireless sensor system preferably consists of three parts: (a) computer software, which initiates the measurement cycle, receives the data, performs the calculations in order to deduce the value of the parameter from a calibration curve and presents these values in digital and graphical form through a user interface; (b) base station firmware, which performs the RF transmit-receive protocol functions; and (c) sensor node firmware, which performs the RF tasks, and scans and measures the sensors.

Figure 18:
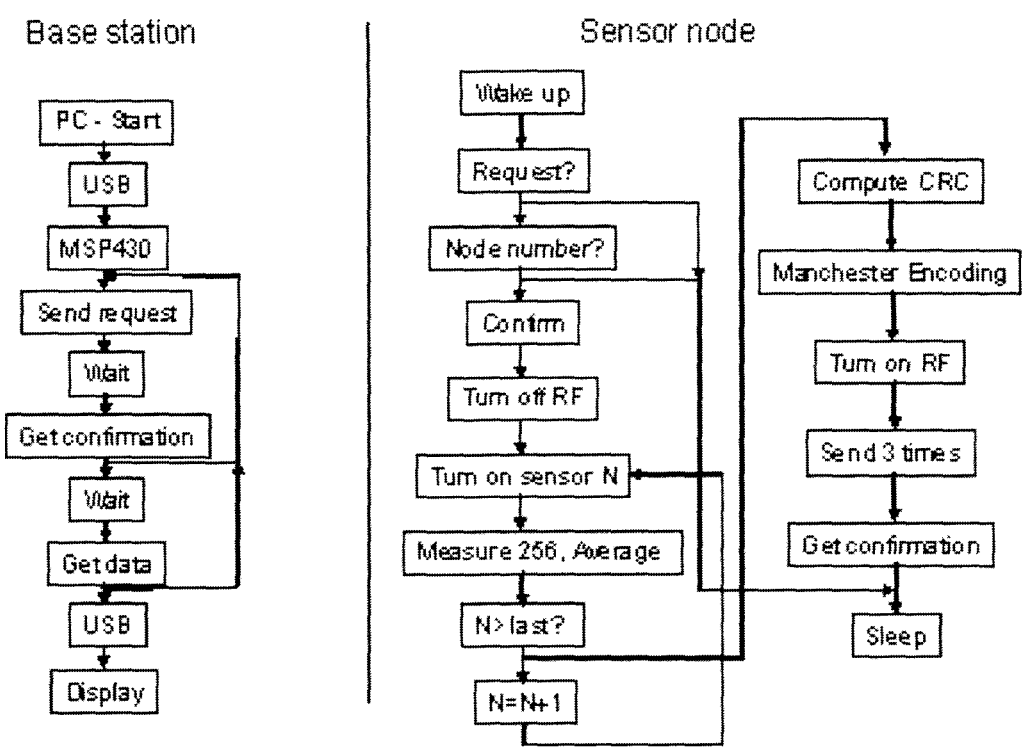
FIG. 18 is a flowchart of protocol flow for communication and data collection in the wireless sensor system, in accordance with one embodiment of the present invention.

The protocol flow is shown in the flowchart of FIG. 18. Every measurement cycle starts with sending the node number that will be polled to the USB serial port. The program uses freely available DLL drivers to send two bytes to a virtual COM port. When the FT245R buffer receives the bytes, its RXF# pin goes low. This generates interrupt on port 2 of MSP430F1121A.

The firmware of the base station 110 waits for the interrupt in low-power mode, after configuring Port 1 as input buffer, and the respective pin on Port 2 as an input. When the interrupt occurs, the firmware comes out of the low power mode and resumes the main loop. It clocks in the two bytes that form the sensor node address, converts them into a word, calculates the Cyclic Redundancy Check (CRC) and encodes the resulting 4 bytes in Manchester encoding for transmission. In one embodiment of the Manchester encoding, transition 0 to 1 is considered 1 and transition 1 to 0 is considered 0. To every byte, a start and stop bits are added. No parity check is added.

Next, the microcontroller switches the multiplexer to access the RF block, turns on the transmitter and configures the pin 14 as an output from Timer A, register 0. The microcontroller then starts the timer and enters a low-power mode. Every time the timer generates an interrupt, it checks the value of the next bit to be transmitted and, if needed, toggles the pin. In this way, a software UART transmitter is realized.

The data that are transmitted consist of a training sequence, two wide stop bits (three times wider than the bits in the training sequence) and the data itself (the node number+CRC byte). Three copies of the data are preferably sent to ensure redundancy and better noise immunity. The training sequence is needed due to the fact that the RX modules constantly produce on their output sequence of 0's and 1's due to the input noise. Sending a long sequence of alternating high and low values (i.e. hex55) allows it to be easily distinguished from the noise (the probability of a noise sequence with the same timing as the 128 consecutive bits is very small).

The base station 110 sends the data and waits for confirmation that the data has been received. If it does not receive a response within 1 second, it sends the data again, and again waits for confirmation. If after 5 attempts there is no confirmation, the base station sends back to the computer the word hexFFFF, which is decoded as "No answer."

At the receiver side of the sensor node, the receiver watches for the width of the received bit. Normally, there is a constant string of bits (measured as transition high-low-high or vice versa) on the RX module input. The microcontroller monitors that sequence and measures the width of the incoming bit. If the width is within the limits for the expected sequence, the microcontroller counts it as a valid bit and expects the next transition. If the bit is again within the time allotted for it, it is also counted as a valid bit, etc.

The microcontroller expects to see a sequence of 122 valid bits in a row. If any of the received bits is not within the specs, the counter of the training sequence is reset and the microcontroller restarts the wait for a valid training sequence. If all of the 122 bits are received, the microcontroller now expects to see two long bits that indicate the start of the data. These long bits are three time the length of the normal bits. If it sees those bits, the microcontroller advances to the next stage; if not, the receiver subroutine is reset and the process starts over.

If both the training sequence and the start bits are correctly identified, the program advances to the next stage where it functions as a software universal asynchronous receiver/transmitter (UART). It receives the transmitted byte following the detection scheme for Manchester encoding. Then, it splits the data in three (the original data were transmitted 3 times) and begins a procedure that is designed to provide crude error correction: the three sequences are compared bitwise. If all the bits are the same, the bit is correctly received. If one of the three bits is different, the value of the bit is considered to be the value of the other two bits. The approach is based on the fact that during radio transmission, the interferences tend to be of burst type and (usually) alter a sequence of bits in one of the bytes. This is especially true at low data rates employed in the device (2.4 kbaud).

After implementing the algorithm (it can yield wrong results if two bits are erroneous) the program calculates CRC. If the CRC confirms the integrity of the data, the microcontroller proceeds further. If not, it clears the registers and waits for the next transmission. The timing of the next transmission is set to accommodate this error correction and checking. The microcontroller finishes the checks before the base station starts the next training sequence and, if everything is OK, sends back confirmation. The program attempts the reception up to 5 times. If it is unsuccessful, it resets.

Once a confirmation has been issued and transmitted back, the sensor node turns off the RF module. This also switches the multiplexer, which now connects the first 3 bits of port 1 to the addressing logic of the light sources and photo detectors.

FIG. 19 is a table showing one possible implementation for the codes for the different light sources and detectors. The multiplexing is done for two reasons: (a) the control algorithm is simpler and avoids possible problems with unintentional switching of the RF; and (b) better utilization of the microcontroller pins.

After issuing the code, the microcontroller measures the output signal from the photodetectors 256 times and averages them. The averaging is done by consecutive addition of every next measurement to a register with carry. After acquisition and summing all the measurements, the result is simply shifted right one byte.

The sensors are scanned consecutively to acquire the measurements from all of them. Then, the data are converted (according to the already described algorithm) in serial format, Manchester encoding, the sensor node number is added and CRC is calculated. The 18 bytes are transmitted back to the base station, which does error correction, CRC check and transmits via USB the results.

The computer program for control initiates the measurement, and serves as a tool for selection of the sensor node and as a visual interface for data display. As it receives the raw measurements from the sensors, it calculates the quantities that are related to the measured values as follows:

Optical density:

$$OD = \lg \frac{I_{ref}}{I_{sig}} \quad (5)$$

pH:

$$pH = \frac{I_{blue}}{I_{violet}} \quad (6)$$

Oxygen:

$$DO_{phase} = \arctan \frac{I_{blue}^{In\text{-}phase}}{I_{blue}^{Quadrature}} - \arctan \frac{I_{orange}^{In\text{-}phase}}{I_{orange}^{Quadrature}} \quad (7)$$

Using the calculated values and the generated calibrations, the software displays the respective measurements of optical density, dissolved oxygen and pH.

The foregoing embodiments and advantages are merely exemplary, and are not to be construed as limiting the present invention. The present teaching can be readily applied to other types of apparatuses. The description of the present invention is intended to be illustrative, and not to limit the scope of the claims. Many alternatives, modifications, and variations will be apparent to those skilled in the art. Various changes may be made without departing from the spirit and scope of the invention, as defined in the following claims. Or example, although the sensor node 120 is shown with a pH sensor 130, an oxygen sensor 140 and a turbidity (OD) sensor 150, it should be appreciated that any number and types of sensors, such as an optical $CO_2$ sensor, may be used in the sensor node 120 while still falling within the scope of the present invention.

What is claimed is:

1. A wireless sensor system for monitoring at least one environmental parameter of a body of water, comprising:
   a base station; and
   at least one buoyant sensor node in wireless communication with the base station, wherein the at least one buoyant sensor node comprises,
      at least one optical sensor for monitoring the at least one environmental parameter of the body of water, wherein the at least one optical sensor comprises at least one optical environmental parameter sensor and at least one light source for generating light that interacts with the at least one optical environmental parameter sensor, and
      a watertight and buoyant enclosure, adapted to float on the body of water, for housing the at least one light source and other electronics associated with the at least one optical sensor, wherein the at least one optical environmental parameter sensor is positioned on an outside surface of the watertight and buoyant enclosure such that it is submerged when the watertight and buoyant enclosure is floating on the body of water.

2. The wireless sensor system of claim 1, wherein the at least one optical sensor comprises:
   an optical pH sensor;
   an optical oxygen sensor; and
   an optical turbidity sensor.

3. The wireless sensor system of claim 2, wherein the optical pH sensor comprises:
   an optically activated pH sensor patch positioned on an outside surface of the watertight and buoyant enclosure;
   a light source positioned within the watertight and buoyant enclosure for generating excitation light for the optically activated pH sensor patch; and
   a detection system positioned within the watertight and buoyant enclosure for detecting emission light from the optically activated pH sensor patch.

4. The wireless sensor system of claim 2, wherein the optical oxygen sensor comprises:
   an optically activated oxygen sensor patch positioned on an outside surface of the watertight and buoyant enclosure;
   a light source positioned within the watertight and buoyant enclosure for generating excitation light for the optically activated oxygen sensor patch; and
   a detection system positioned within the watertight and buoyant enclosure for detecting emission light from the optically activated oxygen sensor patch.

5. The wireless sensor system of claim 2, wherein the turbidity sensor comprises:
   a light source positioned within the watertight and buoyant enclosure for generating a signal light;
   a light guide positioned on an outside surface of the watertight and buoyant enclosure for receiving the signal light, directing the signal light through water surrounding the watertight and buoyant enclosure, and directing the signal light that has passed through the water surrounding the watertight and buoyant enclosure back into the watertight and buoyant enclosure; and a detection system positioned within the watertight and buoyant enclosure for detecting the signal light directed back into the watertight and buoyant enclosure by the light guide.

6. The wireless sensor system of claim 1, wherein the watertight and buoyant enclosure is trapezoidal shaped.

7. The wireless sensor system of claim 6, wherein the watertight and buoyant enclosure is partially filled with a buoyant material.

8. The wireless sensor system of claim 3, wherein the light source comprises:
a blue LED;
a violet LED; and
an excitation filter positioned to receive the outputs from the blue and violet LEDs, wherein the excitation filter passes wavelengths between approximately 400 nm and 480 nm.

9. The wireless sensor system of claim 4, wherein the light source comprises:
a blue LED; and
an excitation filter positioned to receive the output from the blue LED, wherein the excitation filter passes wavelengths between approximately 400 nm and 480 nm.

10. The wireless sensor of claim 8, wherein the detection system comprises:
an emission filter positioned to receive the emission light and transmit filtered light; and
a photodetector positioned to receive the filtered light.

11. The wireless sensor of claim 9, wherein the detection system comprises:
an emission filter positioned to receive the emission light and transmit filtered light; and
a photodetector positioned to receive the filtered light.

12. The wireless sensor of claim 5, wherein the detection system comprises:
an emission filter positioned to receive the signal light directed back into the watertight and buoyant enclosure by the light guide and transmit filtered light; and
a photodetector positioned to receive the filtered light.

13. A sensor node for monitoring at least one environmental parameter of a body of water, comprising:
at least one optical sensor for monitoring the at least one environmental parameter of the body of water, wherein the at least one optical sensor comprises at least one optical environmental parameter sensor and at least one light source for generating light that interacts with the at least one optical environmental parameter sensor;
a wireless communication system for wirelessly transmitting data from the at least one optical sensor; and
a watertight and buoyant enclosure, adapted to float on the body of water, for housing the at least one light source and other electronics associated with the at least one optical sensor and electronics associated with the wireless communication system, wherein the at least one optical environmental parameter sensor is positioned on an outside surface of the watertight and buoyant enclosure such that it is submerged when the watertight and buoyant enclosure is floating on the body of water.

14. The sensor node of claim 13, wherein the at least one optical sensor comprises:
an optical pH sensor;
an optical oxygen sensor; and
an optical turbidity sensor.

15. The wireless sensor system of claim 14, wherein the optical pH sensor comprises:
an optically activated pH sensor patch positioned on an outside surface of the watertight and buoyant enclosure;
a light source positioned within the watertight and buoyant enclosure for generating excitation light for the optically activated pH sensor patch; and
a detection system positioned within the watertight and buoyant enclosure for detecting emission light from the optically activated pH sensor patch.

16. The wireless sensor system of claim 14, wherein the optical oxygen sensor comprises:
an optically activated oxygen sensor patch positioned on an outside surface of the watertight and buoyant enclosure;
a light source positioned within the watertight and buoyant enclosure for generating excitation light for the optically activated oxygen sensor patch; and
a detection system positioned within the watertight and buoyant enclosure for detecting emission light from the optically activated oxygen sensor patch.

17. The wireless sensor system of claim 14, wherein the turbidity sensor comprises:
a light source positioned within the watertight and buoyant enclosure for generating a signal light;
a light guide positioned on an outside surface of the watertight and buoyant enclosure for receiving the signal light, directing the signal light through water surrounding the watertight and buoyant enclosure, and directing the signal light that has passed through the water surrounding the watertight and buoyant enclosure back into the watertight and buoyant enclosure; and
a detection system positioned within the watertight and buoyant enclosure for detecting the signal light directed back into the watertight and buoyant enclosure by the light guide.

18. The wireless sensor system of claim 13, wherein the watertight and buoyant enclosure is trapezoidal shaped.

19. The wireless sensor system of claim 18, wherein the watertight and buoyant enclosure is partially filled with a buoyant material.

20. The wireless sensor system of claim 15, wherein the light source comprises:
a blue LED;
a violet LED; and
an excitation filter positioned to receive the outputs from the blue and violet LEDs, wherein the excitation filter passes wavelengths between approximately 400 nm and 480 nm.

21. The wireless sensor system of claim 16, wherein the light source comprises:
a blue LED; and
an excitation filter positioned to receive the output from the blue LED, wherein the excitation filter passes wavelengths between approximately 400 nm and 480 nm.

22. The wireless sensor of claim 15, wherein the detection system comprises:
an emission filter positioned to receive the emission light and transmit filtered light; and
a photodetector positioned to receive the filtered light.

23. The wireless sensor of claim 16, wherein the detection system comprises:
an emission filter positioned to receive the emission light and transmit filtered light; and
a photodetector positioned to receive the filtered light.

24. The wireless sensor of claim 17, wherein the detection system comprises:

an emission filter positioned to receive the signal light
directed back into the watertight and buoyant enclosure
by the light guide and transmit filtered light; and
a photodetector positioned to receive the filtered light.

* * * * *